(12) United States Patent
Klemarczyk et al.

(10) Patent No.: US 6,627,683 B1
(45) Date of Patent: Sep. 30, 2003

(54) REWORKABLE THERMOSETTING RESIN COMPOSITIONS AND COMPOUNDS USEFUL THEREIN

(75) Inventors: Philip T. Klemarczyk, Canton, CT (US); Lie-Zhong Gong, Bridgewater, NJ (US)

(73) Assignee: Henkel Loctite Corporation, Rocky Hill, CT (US)

( * ) Notice: Subject to any disclaimer, the term of this patent is extended or adjusted under 35 U.S.C. 154(b) by 562 days.

(21) Appl. No.: 09/885,270

(22) Filed: Sep. 5, 2000

(51) Int. Cl.$^7$ .............................. C08K 3/10; C08L 63/02
(52) U.S. Cl. ...................... 523/457; 523/458; 523/466; 528/94; 528/99; 528/103; 528/378; 528/379; 528/380; 549/90; 549/546; 549/555; 549/556; 549/557; 549/561
(58) Field of Search ................................ 523/457, 458, 523/466; 528/94, 99, 103, 378, 379, 380; 549/90, 546, 555, 556, 557, 561

(56) References Cited

U.S. PATENT DOCUMENTS

| | | | |
|---|---|---|---|
| 5,355,580 A | 10/1994 | Tsukada | 29/840 |
| 5,512,613 A | 4/1996 | Afzali-Ardakani et al. | 523/443 |
| 5,560,934 A | 10/1996 | Afzali-Ardakani et al. | 424/497 |
| 5,760,337 A | 6/1998 | Iyer et al. | 174/52.2 |
| 5,783,867 A | 7/1998 | Belke, Jr. et al. | 257/783 |
| 5,872,158 A | 2/1999 | Kuczynski | 522/182 |
| 5,932,682 A | 8/1999 | Buchwalter et al. | 528/94 |
| 5,948,922 A | 9/1999 | Ober et al. | 549/547 |
| 5,973,033 A | 10/1999 | Ober et al. | 523/443 |

FOREIGN PATENT DOCUMENTS

WO 9831738 7/1998

OTHER PUBLICATIONS

Antemou, U.N. et al., "Resoncylic acid–based epoxy compositions", Plasticheskie Massy (1980), (10) p. 17. 1980.*
Abstract of JP5102343, Apr. 1993.*
Abstract of JP5251516, Sep. 1993.*
Abstract of JP6069280, Mar. 1994.*
Abstract of JP6077264, Mar. 1994.*

* cited by examiner

Primary Examiner—Robert Dawson
Assistant Examiner—D. Aylward
(74) Attorney, Agent, or Firm—Steven C. Bauman (57) ABSTRACT

Curable compositions, reaction products of which are reworkable through thermal decomposition, are provided. Specific compounds useful in such curable compositions, as well as curable compositions and thermosets incorporating such compounds, are provided in the present invention. The compounds include a cyclic hydrocarbon moiety including an oxirane or thiirane group and an aromatic ether moiety including an oxirane or thiirane group. The cyclic hydrocarbon moiety and the aromatic ether moiety are joined to each other through an oxycarbonyl-containing linkage or a thiocarbonyl-containing linkage, preferably a secondary or tertiary linkage. Compositions incorporating such compounds are capable of curing by exposure to a specific temperature, and are decomposable at a temperature in excess of the curing temperature, thus providing a composition which is reworkable.

26 Claims, 4 Drawing Sheets

REWORKABLE THERMOSETTING RESIN COMPOSITIONS AND COMPOUNDS USEFUL THEREIN

BACKGROUND OF THE INVENTION

1. Field of the Invention

This invention relates to thermosetting resin compositions useful for mounting semiconductor devices onto a circuit board, such as chip size or chip scale packages ("CSPs"), ball grid arrays ("BGAs"), land grid arrays ("LGAs") and the like, each of which having a semiconductor chip, such as large scale integration ("LSI"), on a carrier substrate. The compositions of this invention are reworkable when subjected to appropriate conditions.

2. Brief Description of Related Technology

In recent years, the popularity of small-sized electronic appliances, such as camera-integrated video tape recorders ("VTRs") and portable telephone sets, has made size reduction of LSI devices desirable. As a result, CSPs, BGAS, and LGAs are being used to reduce the size of packages substantially to that of bare chips. Such CSPs, BGAs, and LGAs improve the characteristics of the electronic device while retaining many of their operating features, thus serving to protect semiconductor bare chips, such as LSIs, and facilitate testing thereof.

Ordinarily, the CSP/BGA/LGA assembly is connected to electrical conductors on a circuit board by use of a solder connection or the like. However, when the resulting CSP/BGA/LGA circuit board structure is exposed to thermal cycling, the reliability of the solder connection between the circuit board and the CSP/BGA/LGA often becomes suspect. Recently, after a CSP/BGA/LGA assembly is mounted on a circuit board, the space between the CSP/BGA/LGA assembly and the circuit board is often now filled with a sealing resin (often referred to as underfill sealing) in order to relieve stresses caused by thermal cycling, thereby improving heat shock properties and enhancing the reliability of the structure.

However, since thermosetting resins are typically used as the underfill sealing material, in the event of a failure after the CSP/BGA/LGA assembly is mounted on the circuit board, it is very difficult to replace the CSP/BGA/LGA assembly without destroying or scrapping the structure in its entirety.

To that end, techniques for mounting a bare chip on a circuit board are accepted as substantially similar to the mounting of a CSP/BGA/LGA assembly onto a circuit board. One such technique, disclosed in Japanese Laid-Open Patent Publication No. 102343/93, involves a mounting process where a bare chip is fixed and connected to a circuit board by use of a photocurable adhesive, where, in the event of failure, this bare chip is removed therefrom. However, this technique is limited to those instances where the circuit board includes a transparent substrate (e.g., glass) which permits exposure to light from the back side, and the resulting structure exhibits poor heat shock properties.

Japanese Laid-Open Patent Publication No. 69280/94 discloses a process where a bare chip is fixed and connected to a substrate by use of a resin capable of hardening at a predetermined temperature. In the event of failure, this bare chip is removed from the substrate by softening the resin at a temperature higher than the predetermined temperature. However, no specific resin is disclosed, and there is no disclosure about treating the resin which remains on the substrate. Thus, the disclosed process is at best incomplete.

As pointed out in Japanese Laid-Open Patent Publication No. 77264/94, it is conventional to use a solvent to remove residual resin from a circuit board. However, swelling the resin with a solvent is a time consuming process and the corrosive organic acid ordinarily used as the solvent may reduce the reliability of the circuit board. Instead, that disclosure speaks to a method for removing residual resin by irradiation with electromagnetic radiation.

Japanese Laid-Open Patent Publication No. 251516/93 also discloses a mounting process using bisphenol A type epoxy resin (CV5183 or CV5183S; manufactured by Matsushita Electric Industrial Co., Ltd.). However, the removal process so disclosed does not consistently permit easy removal of the chip, the curing step is lengthy at elevated temperatures, and the process generally results in poor productivity.

Of course, mechanical methods of removing/replacing semiconductor chips from/on a substrate are known, such as by cutting the chip to be removed/replaced. See U.S. Pat. No. 5,355,580 (Tsukada).

Thermoplastic underfill resins are known for use in semiconductor chip attachment. See U.S. Pat. No. 5,783,867 (Belke, Jr.). However, such thermoplastic resins tend to leak under relatively modest temperature conditions. In contrast, thermosetting resins cure into a matrix which ordinarily have greater thermal stability under end use operating temperatures.

U.S. Pat. No. 5,512,613 (Afzali-Ardakani), U.S. Pat. No. 5,560,934 (Afzali-Ardakani) and U.S. Pat. No. 5,932,682 (Buchwalter), each refer to a reworkable thermoset composition based on a diepoxide component in which the organic linking moiety connecting the two epoxy groups of the diepoxide includes an acid cleavable acyclic acetal group. With such acid cleavable acyclic acetal groups forming the bases of the reworkable composition, a cured thermoset need only be introduced to an acidic environment in order to achieve softening and a loss of much of its adhesiveness.

U.S. Pat. No. 5,872,158 (Kuczynski) refers to thermosetting compositions capable of curing upon exposure to actinic radiation, which are based on acetal diacrylates, and reaction products of which are reported to be soluble in dilute acid.

U.S. Pat. No. 5,760,337 (Iyer) refers to thermally reworkable crosslinked resins to fill the gap created between a semiconductor device and a substrate to which it is attached. These resins are produced by reacting a dienophile (with a functionality greater than 1) with a 2,5-dialkyl substituted furan-containing polymer.

International Patent Publication No. PCT/US98/00858 refers to a thermosetting resin composition capable of sealing underfilling between a semiconductor device including a semiconductor chip mounted on a carrier substrate and a circuit board to which said semiconductor device is electrically connected. The composition includes about 100 parts by weight of an epoxy resin, about 3 to about 60 parts by weight of a curing agent, and about 1 to about 90 parts by weight of a plasticizer. Here, the area around the cured thermoset is to be heated at a temperature of about 190 to about 260° C. for a period of time ranging from about 10 seconds to about 1 minute in order to achieve softening and a loss of much of its adhesiveness.

U.S. Pat. No. 5,948,922 (Ober) and U.S. Pat. No. 5,973,033 (Ober), each refer to a certain class of compounds having tertiary oxycarbonyl linkages, and compositions based on such compounds, which when cured provide decomposable compositions capable of being reworked.

Notwithstanding the state of the art, it would be desirable for an underfilling sealing material to provide good productivity and thermal shock properties at reasonable cost, while allowing the substrates with which it is to be used to be readily processed and easily separated from a semiconductor device without application of acidic media or elevated temperature conditions that may compromise the integrity of the semiconductor devices remaining on the substrate or the substrate itself.

SUMMARY OF THE INVENTION

The present invention is directed to curable compounds useful in curable compositions. The curable compound includes a cyclic hydrocarbon moiety including an oxirane or thiirane group and an aromatic ether moiety including an oxirane or thiirane group. The cyclic hydrocarbon moiety and the aromatic ether moiety are joined to each other through an oxycarbonyl-containing linkage or a thiocarbonyl-containing linkage to form the curable compound, which is thermally cleavable. The curable compound is represented by Formula I as set forth in the Detailed Description of the Invention.

A further aspect of the invention involves curable compositions including such curable compounds. Reaction products of such curable compositions are reworkable through thermal decomposition under exposure to temperature conditions in excess of those used to cure the composition, thus providing the curable compositions with reworkability.

Desirably, the cyclic hydrocarbon moiety of the curable compound which includes an oxirane or thiirane group is a cycloaliphatic epoxy or episulfide, respectively, moiety. Further, the aromatic ether moiety which includes an oxirane or thiirane group is desirably an aromatic glycidyl or thioglycidyl ether, respectively, moiety. Examples of useful compositions are provided herein.

As a further aspect, the curable compositions are particularly useful in thermosetting resin compositions, which are capable of softening and losing their adhesiveness under exposure to temperature conditions in excess of those used to cure the composition. Such curable compositions include a curable resin component, at least a portion of which includes the curable compound containing a cyclic hydrocarbon moiety including an epoxy or episulfide group and an aromatic ether moiety including an epoxy or episulfide group, with the cyclic hydrocarbon moiety and the aromatic ether moiety being joined to each other through an oxycarbonyl-containing linkage or a thiocarbonyl-containing linkage. The curable compositions further include a curing agent component, such as anhydride compounds, amine compounds, amide compounds, imidazole compounds, and combinations thereof, and optionally include an inorganic filler component.

In a particularly useful embodiment, the composition is capable of sealing underfilling between a semiconductor device including a semiconductor chip mounted on a carrier substrate and a circuit board to which the semiconductor device is electrically connected.

The compositions of this invention may also be used for microelectronic applications beyond sealing underfill, such as with glob top, direct chip attachment and other applications for thermosetting compositions. In addition, the compositions may be used in far-flung applications, where thermosetting epoxies, or for that matter other thermosetting or thermoplastic adhesive, coating and sealant compositions, may be used. For instance, the compositions may be used in the assembly of products, whose component parts have value as do the intermediate/finished products, to facilitate assembly and disassembly thereof where defective component parts are found. In that event, the defective component part(s) may be readily removed from the intermediate/finished product(s) and be replaced without having to scrap the entire intermediate/finished product(s). In addition, the speed with which the disassembly may proceed allows throughput to remain high. A non-microelectronic example of such a part is the assembly of prosthetic devices.

DETAILED DESCRIPTION OF THE INVENTION

As noted, the present invention is directed to curable compositions which are reworkable through thermal decomposition. The compositions are capable of curing at a specific temperature, and are decomposable at a temperature in excess of the curing temperature, thus providing a composition which is reworkable. The invention is directed to specific compounds useful in such curable compositions, as well as curable compositions incorporating such compounds.

The compositions of the present invention include a cyclic hydrocarbon moiety including an oxirane or thiirane group, as well as an aromatic ether moiety also including an oxirane or thiirane group. The cyclic hydrocarbon moiety and the aromatic ether moiety are joined to each other through an oxycarbonyl-containing linkage or a thiocarbonyl-containing linkage.

Curable compositions including cycloaliphatic epoxy monomers are capable of decomposing to provide reworkable compositions, but typically require exposure to high temperatures for such decomposition. Other curable compositions which include secondary and tertiary cycloaliphatic epoxy monomers can decompose at lower temperatures, but are expensive to manufacture. The present invention provides compositions which are capable of decomposing at reasonable temperatures and which provide excellent structural characteristics for their intended use at reasonable cost.

Each moiety of the compound may independently include either an epoxy group or an episulfide group. For example, the cyclic hydrocarbon moiety of the present invention desirably includes an oxirane group, such as a cycloaliphatic epoxy moiety. Alternatively, the cyclic hydrocarbon moiety may include a thiirane group, such as a cycloaliphatic episulfide moiety. Also, the aromatic ether moiety of the present invention desirably includes an oxirane group, such as an aromatic glycidyl ether moiety. Alternatively, the aromatic ether moiety may include a thiirane group, such as an aromatic thioglycidyl ether moiety.

Compounds useful in the present invention are defined by the following formula:

I where R is selected from hydrogen, methyl, ethyl, propyl, isopropyl, butyl, isobutyl, tert-butyl, $C_{1-4}$ alkoxy, halogen, cyano, nitro and phenyl; each $R_1$ is independently selected from hydrogen, methyl, ethyl, propyl, and isopropyl; $R_2$ and $R_3$ are independently selected from hydrogen, methyl, ethyl, propyl, phenyl, tolyl, and benzyl; $R_4$ is independently selected from hydrogen, methyl, ethyl, propyl, isopropyl, butyl, isobutyl, tert-butyl, $C_{1-4}$ alkoxy, halogen, cyano, nitro and phenyl; p is an integer from 0–4; and X and Y are independently selected from O and S.

As indicated, Y can be O or S, thus providing the structure with an oxycarbonyl or thiocarbonyl linkage between the cyclic hydrocarbon moiety and the aromatic ether moiety. Desirably, Y is oxygen, producing an ester linkage between the moieties.

Further, at least one of $R_2$ and $R_3$ may be other than hydrogen, producing a secondary linkage between the cycloaliphatic moiety and the aromatic ether moiety. More desirably, neither $R_2$ nor $R_3$ are hydrogen, producing a tertiary linkage between the cycloaliphatic moiety and the aromatic moiety. Without wishing to be bound by any particular theory, it is believed that the secondary and tertiary linkages provide the monomers with the capability of decomposing at low temperatures, thus imparting reworkability to the compounds.

Examples of particularly desirable compounds within Formula I are those having the following structures:

Such compounds can be prepared by reacting acid chlorides including an aromatic linkage with alcohols including a cycloaliphatic moiety. For example, these compounds can be prepared from diene esters or thioesters including an aromatic glycidyl ether moiety and a cycloaliphatic moiety having the following formula:

where R is selected from hydrogen, methyl, ethyl, propyl, isopropyl, butyl, isobutyl, tert-butyl, $C_{1-4}$ alkoxy, halogen, cyano, nitro and phenyl; each $R_1$ is independently selected from hydrogen, methyl, ethyl, propyl, and isopropyl; $R_2$ and $R_3$ are independently selected from hydrogen, methyl, ethyl, propyl, phenyl, tolyl, and benzyl; $R_4$ is independently selected from hydrogen, methyl, ethyl, propyl, isopropyl, butyl, isobutyl, tert-butyl, $C_{1-4}$ alkoxy, halogen, cyano, nitro and phenyl; Y is selected from O or S; and p is an integer from 0–4. Such diene esters are themselves the condensation reaction product of a cycloaliphatic alcohol within the formula:

where R, $R_1$, $R_2$, and $R_3$ are as defined above, with an aromatic acid chloride within the formula:

where $R_4$ and p are as defined above. The condensation is typically performed in an anhydrous polar solvent at a temperature ranging from 0 to about 20° C. for a time period ranging from 6 to 18 hours.

To epoxidize the diene ester or thioester thus formed, a peracid (such as peracetic acid, perbenzoic acid, meta-chloroperbenzoic acid, and the like) may be used, with the reaction carried out until epoxidation of diene ester occurs, typically within a period of time of from 2 to 18 hours.

To form an episulfide from the diene ester or thioester, an epoxidized compound may be used, such as is formed above, and reacted with a thiourea to replace the epoxide linkage with an episulfide linkage. These reactions are generally well known, (e.g., U.S. Pat. No. 3,378,522 to Martin).

As indicated, the present invention is directed to specific compounds which are inventive monomers themselves incorporating a cyclic hydrocarbon moiety and an aromatic ether moiety joined to each other through an oxycarbonyl-containing linkage or thiocarbonyl-containing linkage. The invention is further directed to curable compositions including such compounds. For example, since the curable compounds of the present invention include both a cyclic hydrocarbon moiety and an aromatic ether moiety, such compounds are capable of polymerizing with a number of compounds, including other compounds having such moieties. As such, the curable compounds including a cyclic hydrocarbon moiety and an aromatic ether moiety as described above may be combined with other curable compounds, such as cycloaliphatic epoxy or episulfide compounds, or aromatic glycidyl or thioglycidyl ether compounds, to provide a curable resin. Moreover, the curable compounds of the present invention may also be used as comonomers to crosslink other curable compounds, such as cycloaliphatic epoxy or episulfide compounds and aromatic glycidyl or thioglycidyl ether compounds, to provide a curable resin. Thus, the present invention is further directed to curable compositions including compounds having both a cyclic hydrocarbon moiety and an aromatic ether moiety, as combined with other curable compounds, including cycloaliphatic epoxy or episulfide compounds, aromatic glycidyl or thioglycidyl ether compounds, and mixtures thereof.

Still further, as noted above, the compounds of the present invention are particularly useful in curable compositions, such as thermosetting resin compositions which are useful as underfill sealants between a semiconductor device and a circuit board to which the semiconductor device is electrically connected. Thus, in a further aspect of the present invention, a thermosetting resin composition is provided, which includes broadly (a) a curable resin component, a portion of which is a compound including both a cyclic hydrocarbon moiety having an epoxy or episulfide group and an aromatic ether moiety having an epoxy or episulfide group with the cyclic hydrocarbon moiety and the aromatic ether moiety joined together through an oxycarbonyl linkage or thiocarbonyl linkage, as discussed in detail above; (b) an optional inorganic filler component; and (c) a curing agent component including an anhydride component, a nitrogen-containing component, such as an amine compound, an amide compound, and/or an imidazole compound, and/or combinations thereof. Reaction products of these compositions are capable of softening under exposure to elevated temperature conditions, such as in excess of the temperature chosen to cure the composition. Loss of adhesion to the substrate occurs at temperatures greater than that which was used to cure the composition. For instance, a sufficient amount of adhesion is typically lost at temperatures in excess of about 200° C.

In such an embodiment relating to thermosetting compositions, the presence in the curable resin component of the curable compound including a cyclic hydrocarbon moiety and an aromatic ether moiety joined through an oxycarbonyl or thiocarbonyl linkage, as described, allows for repair, replacement, recovery and/or recycling of operative electronic components from assemblies that have become at least in part inoperative.

Further, such thermosetting resin compositions typically include about 10 to about 60 weight percent of the resin component by weight of the total composition, of which about 25 to about 75 weight percent thereof is comprised of the curable compound including a cyclic hydrocarbon moiety and an aromatic ether moiety; about 0 to about 60 weight percent of the inorganic filler component; and 0.01 to about 110 weight percent of the curing agent component, of which about 0 to about 110 weight percent thereof is comprised of an anhydride compound, and about 0.01 to about 10 weight percent thereof is comprised of a nitrogen-containing component, for example 0.01 to about 10 weight percent of an imidazole compound.

Of course, depending on the particular set of properties desirable for a composition destined for a specific purpose, these values may vary somewhat. Such variation may be achieved without undue experimentation by those persons skilled in the art, and accordingly are contemplated within the scope of the present invention.

As set forth above, the compound including the cycloaliphatic moiety and the aromatic either moeity is desirably selected from epoxy compounds, episulfide compounds, and compounds having both such functional groups. When such curable compound includes epoxy groups, the curable resin component may desirably be an epoxy-based resin component, and may further include any common epoxy resin, such as a multifunctional epoxy resin, in addition to the curable compound including the cycloaliphatic moiety and the aromtic ether moiety. Ordinarily, the multifunctional epoxy resin should be included in an amount within the range of about 15 weight percent to about 75 weight percent of the total of the curable resin component. In the case of bisphenol-F-type epoxy resin, desirably the amount thereof should be in the range of from about 35 to about 65 weight percent, such as about 40 to about 50 weight percent of the total of the curable resin component.

Examples of the multifunctional epoxy resin include bisphenol-A-type epoxy resin, bisphenol-F-type epoxy resin (such as RE-404-S from Nippon Kayaku, Japan), phenol novolac-type epoxy resin, and cresol novolac-type epoxy resin (such as "ARALDITE" ECN 1871 from Ciba Specialty Chemicals, Hawthorne, N.Y.).

Other suitable epoxy resins include polyepoxy compounds based on aromatic amines and epichlorohydrin, such as N,N,N',N'-tetraglycidyl-4,4'-diaminodiphenyl methane; N-diglycidyl-4-aminophenyl glycidyl ether; and N,N,N',N'-tetraglycidyl-1,3-propylene bis-4-aminobenzoate.

Among the epoxy resins suitable for use herein also include polyglycidyl derivatives of phenolic compounds, such as those available commercially under the tradename "EPON", such as "EPON" 828, "EPON" 1001, "EPON" 1009, and "EPON" 1031 from Shell Chemical Co.; "DER" 331, "DER" 332, "DER" 334, and "DER" 542 from Dow Chemical Co.; and BREN-S from Nippon Kayaku. Other suitable epoxy resins include polyepoxides prepared from polyols and the like and polyglycidyl derivatives of phenol-formaldehyde novolacs, the latter of which are available commercially under the tradename "DEN", such as "DEN" 431, "DEN" 438, and "DEN" 439 from Dow Chemical. Cresol analogs are also available commercially under the tradename "ARALDITE", such as "ARALDITE" ECN 1235, "ARALDITE" ECN 1273, and "ARALDITE" ECN 1299 from Ciba Specialty Chemicals Corporation. SU-8 is a bisphenol-A-type epoxy novolac available from Interez, Inc. Polyglycidyl adducts of amines, aminoalcohols and polycarboxylic acids are also useful in this invention, commercially available resins of which include "GLYAMINE" 135, "GLYAMINE" 125, and "GLYAMINE" 115 from F.I.C. Corporation; "ARALDITE" MY-720, "ARALDITE" 0500, and "ARALDITE" 0510 from Ciba Specialty Chemicals and PGA-X and PGA-C from the Sherwin-Williams Co.

Examples of cycloaliphatic epoxy resins include those available commercially under the tradenames ERL-4221, ERL-4299, ERL-4206 and ERL-4234, as well as vinylcyclohexene monoxide, all of which are available from Union Carbide Corporation.

And, of course, combinations of the different epoxy resins are also desirable for use herein.

When the curable compound includes episulfide groups, the curable resin component may desirably be the partial or complete episulfide counterpart to the epoxy resins noted above. As an inorganic filler component, many materials are potentially useful. For instance, the inorganic filler component may often include reinforcing silicas, such as fused silicas, and may be untreated or treated so as to alter the chemical nature of their surface. Virtually any reinforcing fused silica may be used.

Particularly desirable ones have a low ion concentration and are relatively small in particle size (e.g., in the range of about 2–10 microns, such as on the order of about 2 microns), such as the silica commercially available from Admatechs, Japan under the trade designation SO-E5.

Other desirable materials for use as the inorganic filler component include those constructed of or containing aluminum oxide, silicon nitride, aluminum nitride, silica-coated aluminum nitride, boron nitride and combinations thereof.

The curing agent component should include materials capable of catalyzing the polymerization of the curable resin component of the inventive compositions. Desirable curing agents for use with the present invention include an anhydride component, a nitrogen-containing component, such as an amine compound, an amide compound, and an imidazole compound, and combinations thereof.

Appropriate anhydride compounds for use herein include mono- and poly-anhydrides, such as hexahydrophthalic anhydride ("HHPA") and methyl hexahydrophthalic anhydride ("MHHPA") (commercially available from Lindau Chemicals, Inc., Columbia, S.C., used individually or as a combination, which combination is available under the trade designation "LINDRIDE" 62C) and 5-(2,5-dioxotetrahydrol)-3-methyl-3-cyclohexene-1,2-dicarboxylic anhydride (commercially available from ChrisKev Co., Leewood, Kans. under the trade designation B-4400).

Of course, combinations of these anhydride compounds are also desirable for use in the compositions of the present invention.

Examples of the amine compounds include aliphatic polyamines, such as diethylenetriamine, triethylenetetramine and diethylaminopropylamine; aromatic polyamines, such as m-xylenediamine and diaminodiphenylamine; and alicyclic polyamines, such as isophoronediamine and menthenediamine.

In particularly desirable embodiments of the present invention, aromatic polyamines and alicyclic polyamines are desirable as curing agents, particularly 4,4'-methylenedianiline ("MDA") and 4,4'methylenebis (cyclohexylamine) ("MCA"). Of course, combinations of these amine compounds are also desirable for use in the compositions of the present invention.

Examples of amide compounds include cyano-functionalized amides, such as dicyandiamide.

The imidazole compounds may be chosen from imidazole, isoimidazole, and substituted imidazoles, such as alkyl-substituted imidazoles (e.g., 2-methyl imidazole, 2-ethyl-4-methylimidazole, 2,4-dimethylimidazole, butylimidazole, 2-heptadecenyl-4-methylimidazole, 2-methylimidazole, 2-undecenylimidazole, 1-vinyl-2-methylimidazole, 2-n-heptadecylimidazole, 2-undecylimidazole, 2-heptadecylimidazole, 2-ethyl 4-methylimidazole, 1-benzyl-2-methylimidazoie, 1-propyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-guanaminoethyl-2-methylimidazole and addition products of an imidazole and trimellitic acid, 2-n-heptadecyl-4-methylimidazole and the like, generally where each alkyl substituent contains up to about 17 carbon atoms and desirably up to about 6 carbon atoms), and aryl-substituted imidazoles [e.g., phenylimidazole, benzylimidazole, 2-methyl-4,5-diphenylimidazole, 2,3,5-triphenylimidazole, 2-styrylimidazole, 1-(dodecyl benzyl)-2-methylimidazole, 2-(2-hydroxyl-4-t-butylphenyl)-4,5-diphenylimidazole, 2-(2-methoxyphenyl)-4,5-diphenylimidazole, 2-(3-hydroxyphenyl)-4,5-diphenylimidazole, 2-(p-dimethylaminophenyl)-4,5-diphenylimidazole, 2-(2-hydroxyphenyl)-4,5-diphenylimidazole, di(4,5-diphenyl-2-imidazole)-benzene-1,4,2-napnthyl-4,5-diphenylimidazole, 1-benzyl-2-methylimidazole, 2-p-methoxystyrylimidazole, and the like, generally where each aryl substituent contains up to about 10 carbon atoms and desirably up to about 8 carbon atoms].

Examples of commercial imidazole compounds are available from Air Products, Allentown, Pa. under the trade designation "CUREZOL" 1B2MZ and from Synthron, Inc., Morganton, N.C. under the trade designation "ACTIRON" NXJ-60; and from Borregaard Synthesis, Newburyport, Mass. under the trade designation "CURIMID CN".

Of course, combinations of these imidazole compounds are also desirable for use in the compositions of the present invention.

The curing agent component may be used in an amount of from about 0.01 to about 110 parts by weight per 100 parts of the curable resin, desirably for the anhydride component, the amount may be 0 to about 110 parts, such as about 3 to about 60 parts, by weight per 100 parts of the curing agent component. For the nitrogen-containing component, the amount may be about 0.01 to about 10 parts, such as about 2 to about 5 parts, by weight per 100 parts of the curing agent component.

In addition, the composition may also include a flowability agent, such as a silane and/or titanate.

Appropriate silanes for use herein include octyl trimethoxy silane (commercially available from OSI Specialties Co., Danbury, Conn. under the trade designation A-137), and methacryloxy propyl trimethoxy silane (commercially available from OSI under the trade designation A-174).

Appropriate titanates for use herein include titanium IV tetrakis [2,2-bis[(2-propenyloxy)methyl]-1-butanolato-0] [bis(ditridecylphosphito-0), dihydrogen]$_2$ (commercially available from Kenrich Petrochemical Inc., Bayonne, N.J. under the trade designation KR-55).

When used, the flowability agent may be used in an amount of 0 to about 2 parts by weight per 100 parts of the curable resin.

In addition, adhesion promoters, such as the silanes, glycidyl trimethoxysilane (commercially available from OSI under the trade designation A-187) or gamma-amino propyl triethoxysilane (commercially available from OSI under the trade designation A-1100), may be used.

Conventional cyanate esters may also be used in the inventive compositions, which are disclosed in U.S. Pat. No. 4,477,629 and 4,528,366, UK Patent No. 1,305,702 and International Patent Publication WO 85/02184.

When used, the cyanate esters may be used in an amount of about 1 to about 20 weight percent based on the total amount of the curable resin component.

Conventional additives may also be used in the compositions of the present invention to achieve certain desired physical properties of the composition, the cured reaction product, or both.

For instance, it may be desirable in certain instances (particularly where a large volume of inorganic filler component is used) to include a reactive co-monomer component for the curable resin component, such as a reactive diluent.

Appropriate reactive diluents for use herein may include monofunctional or certain multifunctional curable resins. The reactive diluent should have a viscosity which is lower than that of the curable resin component. Ordinarily, the reactive diluent should have a viscosity less than about 250 cps. In the event such a monofunctional resin is included as a reactive diluent, such resin should be employed in an amount of up to about 50 parts based on the total of the curable resin component.

When epoxy-based resin compositions are used, the monofunctional epoxy resin should have an epoxy group with an alkyl group of about 6 to about 28 carbon atoms, examples of which include $C_{6-28}$ alkyl glycidyl ethers, $C_{6-28}$ fatty acid glycidyl esters and $C_{6-28}$ alkylphenol glycidyl ethers.

Commercially available monofunctional epoxy resin reactive diluents include those from Pacific Epoxy Polymers, Richmond, Mich., under the trade designations PEP-6770 (glycidyl ester of neodecandoic acid), PEP-6740 (phenyl glycidyl ether) and PEP-6741 (butyl glycidyl ether).

Commercially available multifunctional epoxy resin reactive diluents include those from Pacific Epoxy Polymers, under the trade designations PEP-6752 (trimethylolpropane triglycidyl ether) and PEP-6760 (diglycidyl aniline).

The compositions of the present invention may further contain other additives, such as defoaming agents, leveling agents, dyes, and pigments. Moreover, photopolymerization initiators may also be incorporated therein, provided that such initiators do not adversely affect the properties of the composition or reaction products formed therefrom.

The thermosetting resin compositions of the present invention may be of the one-pack type, in which all the ingredients are mixed together, or of the two-pack type in which the curable component(s) is(are) included in one part and the curing agent is stored separately in a second part, and mixed together only prior to use.

During application, the thermosetting resin compositions according to the present invention penetrate and flow readily into the space between the semiconductor chip and the circuit board, or at least show a reduction in viscosity under heated or use conditions thus penetrating and flowing easily.

Generally, it is desirable to prepare thermosetting resin compositions of this invention by selecting the types and proportions of various components to reach a viscosity at a temperature of 25° C. in the range of 500 to 70,000 cps, such as 800 to 3,000 cps, depending on the amount present (if any) of an inorganic filler component, so as to improve its ability to penetrate into the space (e.g., of 10 to 200 $\mu$m) between the circuit board and the semiconductor device. At this viscosity, the gel times of the compositions will also be tailored to a specified period of time (such as 15 seconds, or 1 or 2 minutes) at a temperature of about 150° C. In such case, the inventive compositions should show no or substantially no increase of viscosity after a period of time of about six hours under ambient temperature conditions. With such a gel time, the compositions penetrate into the space (e.g., of 10 to 200 $\mu$m) between the circuit board and the semiconductor device relatively rapidly, and allow for a greater number of assemblies to be filled without observing a viscosity increase in the composition thereby rendering it less effective for application.

The cured thermosets of the invention are thermally decomposable by heating to a temperature above the curing temperature and below about 260° C., desirably below about 220° C. At such temperatures, the cured thermosets lose their polymerization structure, and decompose to produce the reworkable aspect of the invention.

Figure 1:
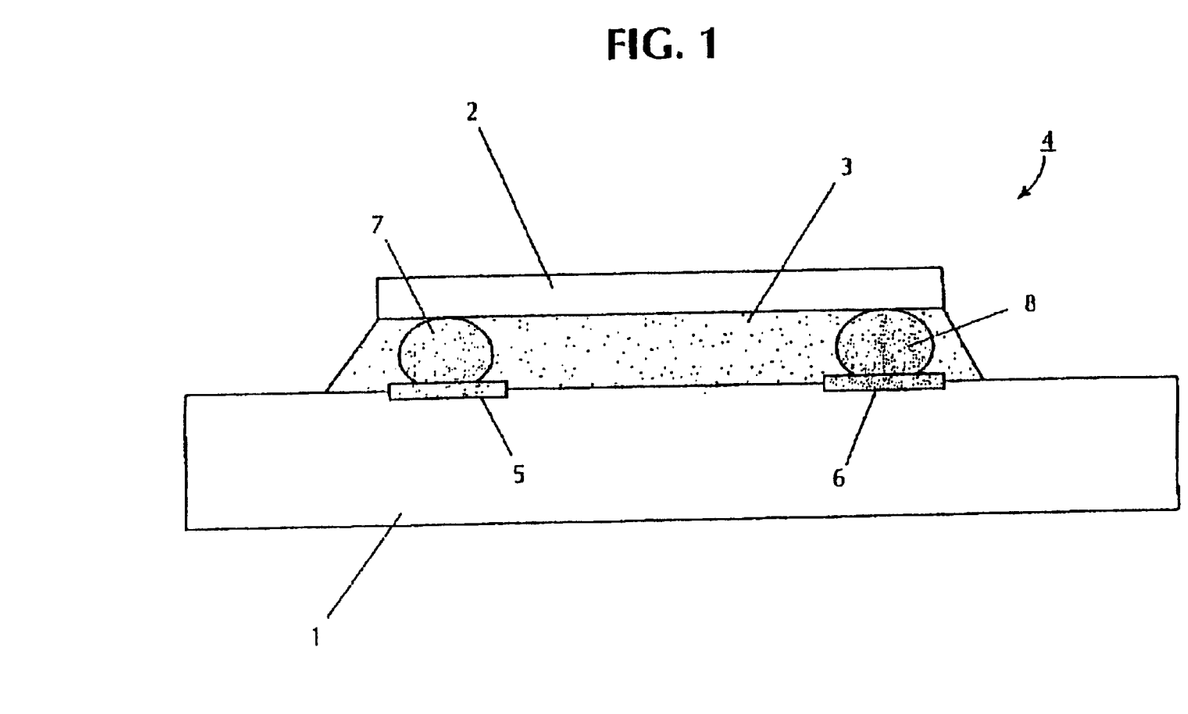
FIG. 1 depicts a cross-sectional view showing an example of the mounting structure in which the thermosetting resin composition of the present invention is used.

Reference to FIG. 1 shows a mounted structure (i.e., an FC package) in which a thermosetting resin composition of the present invention has been applied and cured.

The FC package 4 is formed by connecting a semiconductor chip (a bare chip) 2 to a carrier substrate 1 (e.g., a circuit board) and sealing the space therebetween suitably with a thermosetting resin composition 3.

More specifically, for example, in the assembly of FC semiconductor devices using SBB technology, the semiconductor chip 2 may be passed over a substrate bearing a conductive adhesive paste (such as a metal-filled epoxy) to form a layer thereof on the semiconductor chip 2. The layer is ordinarily formed by a printing mechanism. The conductive adhesive paste may be applied on either the carrier substrate or the semiconductor chip. One way to do this is with the stencil claimed and described in International Patent Publication No. PCT/FR$_{95/00898}$. Alternatively, this connection may also be made by an anisotropically conductive adhesive. See International Patent Publication No. PCT/US97/13677.

Thereafter, the semiconductor chip 2 is positioned over the carrier substrate 1 in such a manner so that the semiconductor chip 2 is in alignment with the electrodes 5 and 6 on the carrier substrate 1, now coated with a patterned layer of conductive adhesive paste or solder 7 and 8. The conductive adhesive paste may be cured by a variety of ways, though ordinarily a heat cure mechanism is employed.

In order to improve reliability, the space between the semiconductor chip 2 and the carrier substrate 1 is sealed with a thermosetting resin composition 3. The cured product of the thermosetting resin composition should completely fill that space.

The semiconductor chip ordinarily may be coated with a polyimide-, benzocyclobutane- or silicone nitride-based material to passivate environmental corrosion.

Carrier substrates may be constructed from ceramic substrates of $Al_2O_3$, $SiN_3$ and mullite ($Al_2O_3$—$SiO_2$); substrates or tapes of heat-resistant resins, such as polyimides; glass-reinforced epoxy; ABS and phenolic substrates which are also used commonly as circuit boards; and the like. Any electrical connection of the semiconductor chip to the carrier substrate may be used, such as connection by a high-melting solder or electrically (or anisotropically) conductive adhesive and the like. In order to facilitate connections, particularly in SBB technology, the electrodes may be formed as wire bond bumps.

After the semiconductor chip is electrically connected to the carrier substrate, the resulting structure is ordinarily subjected to a continuity test or the like. After passing such test, the semiconductor chip may be fixed thereto with a thermosetting resin composition, as described below. In this way, in the event of a failure, the semiconductor chip may be removed before it is fixed to the carrier substrate with the thermosetting resin composition.

Using a suitable application means, such as a dispenser, a thermosetting resin composition in accordance with this invention is applied to the periphery of the electronically-connected semiconductor chip. The composition penetrates by capillary action into the space between the carrier substrate and the semiconductor chip.

The thermosetting resin composition is then thermally cured by the application of heat. During the early stage of this heating, the thermosetting resin composition shows a significant reduction in viscosity and, hence, an increase in fluidity, so that it more easily penetrates into the space between the carrier substrate and the semiconductor chip. Moreover, by preheating the carrier substrate, the thermosetting resin composition is allowed to penetrate fully into the entire space between the carrier substrate and the semiconductor chip.

Thermosetting resin compositions of the present invention may ordinarily be cured by heating to a temperature in the range of about 120 to about 180° C. for a period of time of about 0.5 to 30 minutes. However, generally after application of the composition, an initial cure time of about 1 minute sets up the composition, and complete cure is observed after about 5 to about 15 minutes at 150° C. Thus, the composition of the present invention can be used at relatively moderate temperatures and short-time curing conditions, and, hence, achieve very good productivity.

The amount of thermosetting resin composition applied should be suitably adjusted so as to fill almost completely the space between the carrier substrate and the semiconductor chip, which amount may vary depending on application.

Cured reaction products of the thermosetting resin compositions of the present invention demonstrate excellent adhesive force, heat resistance and electric properties, and acceptable mechanical properties, such as flex-cracking resistance, chemical resistance, moisture resistance and the like, for the applications for which they are used herein.

In the mounting process by using the thermosetting resin composition of the present invention, after the semiconductor device is mounted on the circuit board as described above, the resulting structure is tested with respect to characteristics of the semiconductor device, connection between the semiconductor device and the circuit board, other electrical characteristics, and the state of sealing. In the event a failure is found, repair can be made in the following manner and as shown in the flow diagram depicted in FIG. 2.

The area around the semiconductor device which has failed is heated at a temperature of about 190 to about 260° C. for a period of time ranging from about 10 seconds to about 1 minute. (See FIG. 2, step 1.) Desirably, the temperature should be maintained in the range of about 210° to about 220° C. and the period of time should be within the 30 seconds to 1 minute range. Although no particular limitation is placed on the way in which heating occurs, localized heating is particularly desirable, such as the application of hot air to the failure site by a heating gun.

Figure 2:
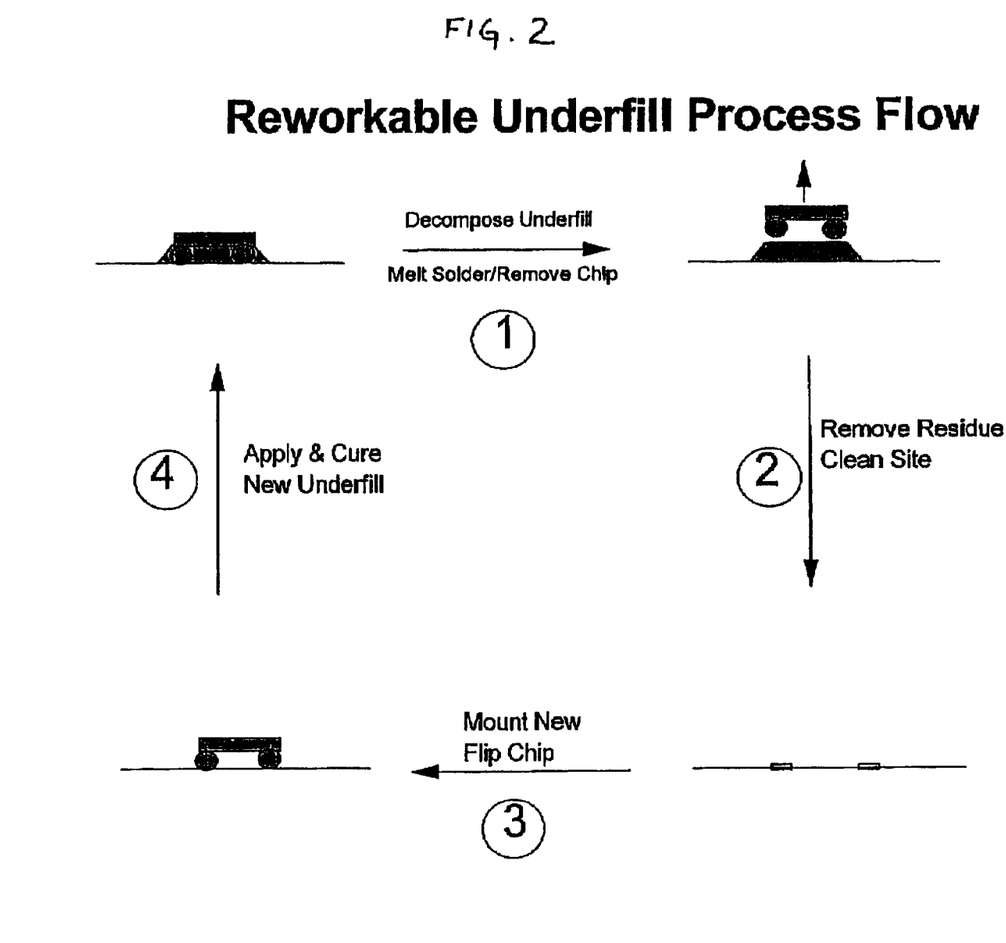
FIG. 2 depicts a flow diagram of a procedure useful to rework a cured thermosetting resin composition in accordance with the present invention, so as to remove a semiconductor device from a circuit board to which it had been attached.

As soon as the solder is melted and the resin is softened by partial decomposition to cause a reduction in bond strength, the semiconductor device may be pulled apart and removed from the substrate, such as with tweezers or pliers.

After the semiconductor device 4 is removed, a residue of the cured reaction product of the thermosetting resin composition and a residue of the solder are left on the circuit board 5. The residue of the cured product of the thermosetting resin composition can be removed, for example, by scraping it off after the residue has been softened by heating it to a predetermined temperature.

The residue of the solder can be removed, for example, by use of a solder-absorbing braided wire. (See FIG. 2, step 2.)

Finally, a new semiconductor chip may be mounted again onto the circuit board (which has been cleaned as described above) in the manner as described above. (See FIG. 2, step 3.) Following mounting, a thermosetting resin composition in accordance with this invention may be dispensed in the area between the semiconductor device and the circuit board. (See FIG. 2, step 4.) Repair of the failure site is thus completed.

Where a failure site is found in the circuit board, the semiconductor device can be reused by removing the residue of the cured reaction product of the thermosetting resin composition and the residue of the solder left on the bottom of the semiconductor device in the same manner as described above.

The present invention will be more readily appreciated with reference to the examples which follow.

EXAMPLE 1

In the following example, compositions in accordance with the present invention were prepared and evaluated for performance in view of comparative compositions.

Synthesis of Glycidyl Ether Cycloaliphatic Epoxide (GECE)

All glassware was dried in an oven at 120° C. overnight and cooled to room temperature under nitrogen prior to use.
Preparation of 4-(Allyloxy) Benzoic Acid 3750 ml of ethanol and 98.75 grams of potassium hydroxide (1.75 mol) were combined in a 5000 ml three-necked reaction flask, equipped with a magnetic stirrer, a thermometer, a condenser and an addition funnel. After the potassium hydroxide dissolved, 93.75 grams of 4-hydroxybenzoic acid (0.675 mol) and 1.25 grams of potassium iodide were added to the solution. The solution was then heated to reflux, and 81.75 grams of allyl bromide (0.675 mol) was added dropwise to the solution and refluxed overnight. A total of 2000 ml of solvent was then distilled out of the reactor. A layer of solid potassium bromide collected on the internal wall of the flask. The remaining mixture was cooled to room temperature, poured into 2500 ml of water, and neutralized with 6 N aqueous hydrochloric acid. The product precipitated, was filtered, and was washed with deionized water. The crude product was dried under vacuum at 110° C., recrystallized from ethanol (400 ml), and dried again under vacuum, to provide allyloxy benzoic acid.

Synthesis of Allyloxybenzoic Acid Chloride

To a 2000 ml four-necked reaction flask, equipped with a magnetic stirrer, thermometer, addition funnel, condenser and a nitrogen sweep, was added 281 grams of thionyl chloride (2.38 moles), 1 ml of dimethyl formamide, and 1000 ml of toluene. 356 grams of the allyloxybenzoic acid (2.0 moles) as prepared above was added over approximately 20 minutes. The reaction temperature was kept below 20° C. with an ice/water bath. The nitrogen sweep was connected to a trap, which contained 1000 ml of a 4 M aq. NaOH solution to react with $SO_2$ and HCl that are formed during the reaction. After the addition was complete, the solution was stirred for 3 hours at room temperature and then heated to reflux. After 3.5 hours of reflux, it was cooled to room temperature. Solvent was distilled at atmospheric pressure because removal under reduced pressure caused severe bumping. After most of the solvent was removed, the residue was transferred to a 1000 ml flask equipped with a distillation head. The product was then vacuum distilled.

Synthesis of Diene Ester

26.2 grams of A-terpineol (170 mmol) and 150 ml of anhydrous tetrahydrofuran (THF) were combined in a 500 ml four-necked reaction flask, equipped with a magnetic stirrer, a thermometer, a condenser, an addition funnel, and a nitrogen sweep. The reactor was cooled to below 5° C. using an ice/water bath. 100 ml of n-butyl lithium in hexane (160 mmol) was transferred to the additional funnel by syringe, and was added into the reactor dropwise with stirring. After the addition of the n-butyl lithium solution was complete, the reaction temperature was raised to room temperature, and the reaction mixture was stirred for three hours at room temperature. A yellow solution formed.

After the reaction was complete, the mixture was again cooled to below 5° C., and 24.9 grams of freshly prepared allyloxy benzoic acid chloride (140 mmol) as prepared above was then added dropwise over a 30 minute period. After the addition was complete, the reaction solution was stirred overnight at room temperature. Excess n-butyl lithium was hydrolyzed with the addition of 200 ml water. The organic phase was separated and the aqueous phase was extracted three times with 100 ml of ethyl ether. The combined organic phases were washed once with 250 ml of saturated aqueous sodium bicarbonate ($NaHCO_3$) and 250 ml of saturated aqueous. sodium chloride solutions. The organic phase was dried with magnesium sulfate, filtered, and treated with basic alumina. After filtration, solvent and excess α-terpineol were removed by vacuum distillation. The final product was a pale yellow liquid diene ester.

Epoxidation of Diene Ester

12 grams of the diene ester (40 mmol) was combined in a 500 ml three-necked reaction flask with 120 ml of methylene chloride and 130 ml of a pH 8.0 buffer. The reaction flask was equipped with a mechanical stirrer, a thermometer, and a condenser. The temperature of the solution was cooled to below 5° C. using an ice/water bath. 30 grams of 70% m-chloroperoxybenzoic acid (m-CPBA) (118 mmol) was added to the reaction mixture in small portions over a 20 minute period. The temperature was then raised to ambient and the reaction mixture was stirred for 24 hours. During this period, small amounts of aqueous sodium hydroxide solution (0.1 M) were added to the reaction solution to maintain a pH between 5.5 and 6.0. After stirring for 24 hours, the reaction was incomplete. The reaction temperature was then cooled to below 5° C., and an additional 20 grams of m-CPBA (79 mmol) was added to the reaction mixture in small portions. The reaction was stirred at room temperature for 18 hours, and small portions of aqueous sodium hydroxide (0.1 M) were added to maintain the pH between 5.5 and 6.0. The organic layer was separated and filtered to remove m-chlorobenzoic acid (m-CBA). The organic phase was washed twice each with 200 ml of dilute aqueous sodium sulfite and 200 ml dilute aqueous sodium hydroxide, dried with magnesium sulfate, filtered and treated with basic alumina. After filtration, solvent was removed under reduced pressure to produce a clear viscous liquid of glycidyl ether cycloaliphatic epoxide monomer (GECE).

The following reaction scheme outlines this synthesis:

Formulations

Three monomers, namely an α-terp epoxide, a cycloaliphatic epoxy monomer, and the diglycidyl ether of Bisphenol F, were prepared as comparison monomers having the following chemical structures:

α-terp epoxide cycloaliphatic epoxy monomer diglycidyl ether of Bisphenol F

The three monomers above and the glycidyl ether cycloaliphatic epoxide monomer (GECE) as prepared above were incorporated into separate formulations to produce curable compositions as follows:

Differential Scanning Calorimetry (DSC)

Figure 3:
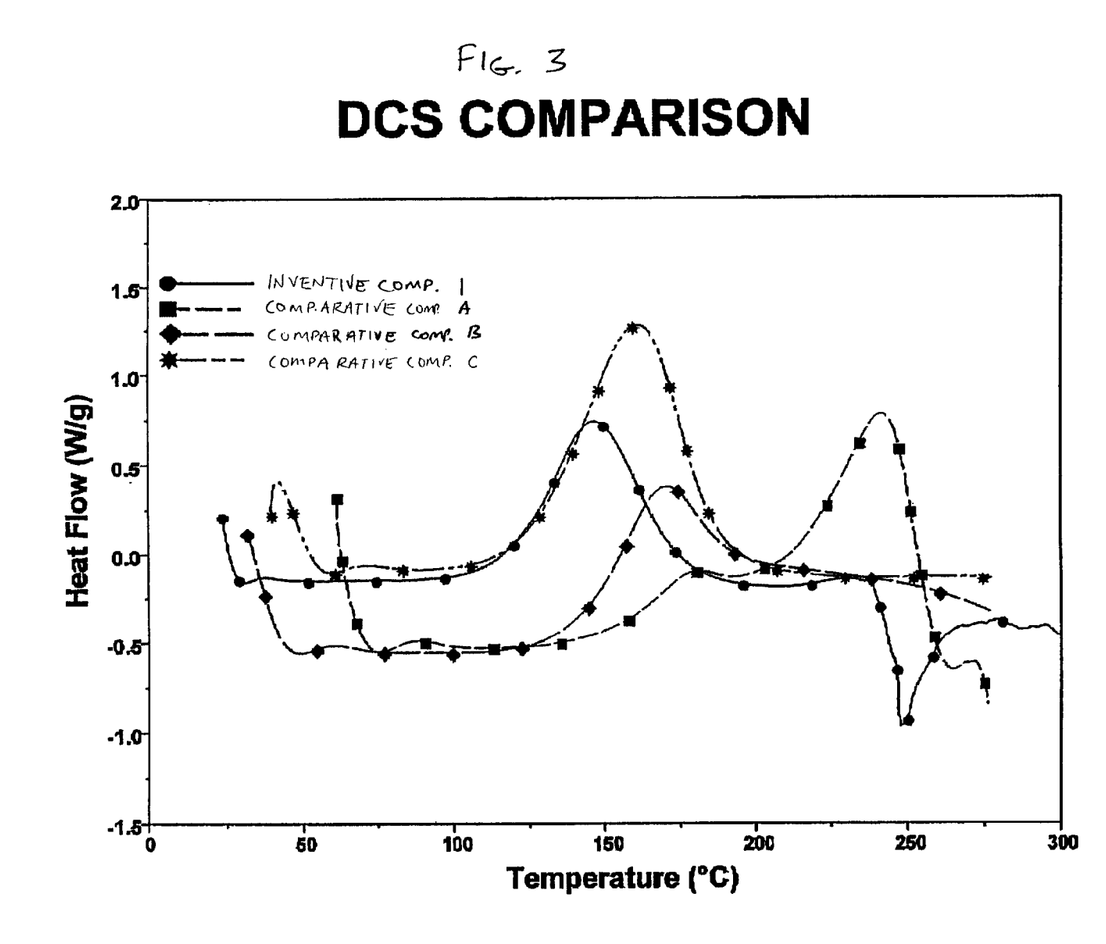
FIG. 3 is a Differential Scanning Calorimetry graph comparing a curable composition in accordance with the present invention with comparative compositions.

Each of Comparative Compositions A, B, and C and Inventive Composition 1 were prepared in the same manner, including mixing of the components as set forth above. Each of the compositions as prepared were subjected to differential scanning calorimetry performed on a TA Instruments Model 2920 Differential Scanning Calorimeter. 10–20 milligrams of each composition was placed in an aluminum sample pan, placed in the DSC sample cell, and heated at 20° C. per minute, up to a temperature of 280° C. The results of the DSC are shown in FIG. 3.

As is apparent, the peak maximum for thermal polymerization of Inventive Composition 1 occurs at a lower temperature than each of Comparative Compositions A, B, and C. Thus, the monomer of Inventive Composition 1 cures at a lower temperature than all of the Comparative Compositions A, B, and C.

Thermogravimetric Analysis (TGA)

Figure 4:
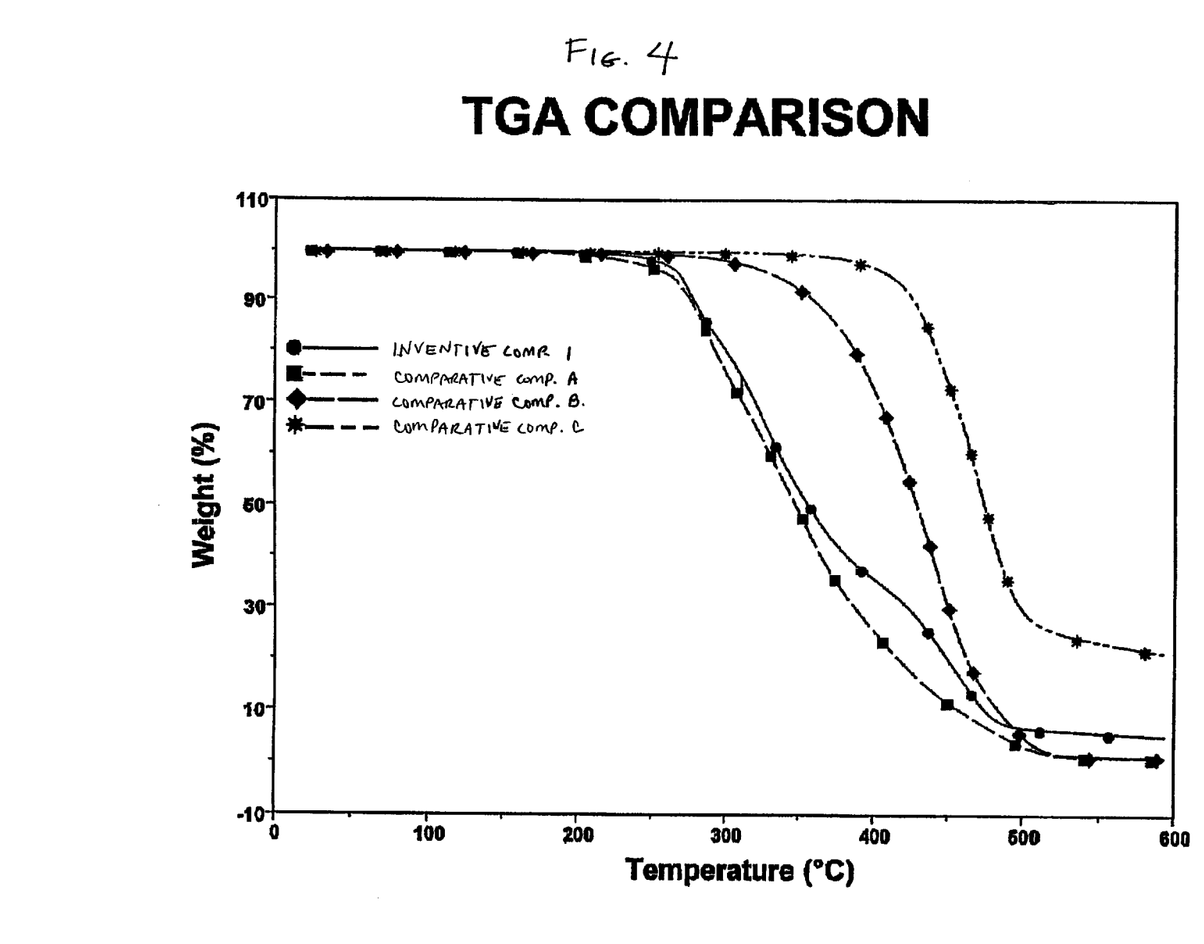
FIG. 4 is a Thermogravimetric Analysis graph comparing a curable composition in accordance with the present invention with comparative compositions.

The components for each of Comparative Compositions A, B, and C and Inventive Composition 1 were mixed as set forth above. 2.0 grams of each formulation were separately prepared in aluminum weighing pans and thermally cured for 2 hours at 100° C. followed by a further cure for 6 hours at 140° C. Subsequently, 10–30 milligrams of the cured compositions were heated in a TA Instruments Model 2950 Thermogravimetric Analyzer at 20° C. per minute, up to a temperature of 600° C. to perform a thermogravimetric analysis (TGA). The results are shown in FIG. 4.

As is apparent, the TGA decomposition profile of Inventive Composition 1 is very similar to that of Comparative Composition A, incorporating α-terp epoxide, and lower than that of Comparative Compositions B and C.

A comparison of the DSC analysis of the Comparative Compositions A, B and C with the Inventive Composition 1 demonstrates that, with the lower cure temperature seen through Inventive Composition 1, complete curing of the thermosetting composition is achieved during the cure cycle with the Inventive Composition 1, as demonstrated through the peak maximum for polymerization. Further, the onset of decomposition is achieved at a lower temperature for Inventive Composition 1, as compared with Comparative Compositions A, B and C, as demonstrated through the TGA analysis.

As a result, it is evident that compositions according to the present invention cure at lower temperatures as compared with known compositions, and decompose at temperatures at least as low as the comparative compositions, thus providing compositions that are reworkable at temperatures at least as low as known compositions. More specifically, the inventive compositions cure at a lower temperature and are controllably degradable at about the same temperature as known compositions, thereby providing a wider temperature difference between cure temperature and rework temperature. This wider temperature difference is important in ensuring that degradation and cure remain distinct physical mechanisms.

The samples described above are presented as illustrative, rather than limiting, examples of the inventive compositions. Many additional embodiments thereof are included in the spirit and scope of the invention, which is defined by the claims.

What is claimed is:

1. A curable composition, reaction products of which are reworkable through thermal decomposition under exposure

| COMPONENT | | Comparative Composition | Comparative Composition | Comparative Composition | Inventive Composition |
|---|---|---|---|---|---|
| Type | Identity | A | B | C | 1 |
| Epoxy Monomer | α-Terp Epoxide | 100 phr | — | — | — |
| | cycloaliphatic epoxy monomer | — | 100 phr | — | — |
| | diglycidyl ether of Bisphenol F | — | — | 100 phr | — |
| | glycidyl ether cycloaliphatic epoxide | — | — | — | 100 phr |
| Curing Agent | Methyl hexahydrophthalic anhydride | 90 phr | 90 phr | 90 phr | 90 phr |
| | Benzyldimethyl amine | 1.5 phr | 1.5 phr | 1.5 phr | 1.5 phr |
| | Ethylene Glycol | 2 phr | 2 phr | 2 phr | 2 phr | phr — parts per hundred to temperature conditions in excess of those used to cure the composition, said curable composition comprising a compound containing a cyclic hydrocarbon moiety including an oxirane or thiirane group and an aromatic ether moiety including an oxirane or thiirane group, said cyclic hydrocarbon moiety and said aromatic ether moiety being joined to each other through an oxycarbonyl-containing linkage or a thiocarbonyl-containing linkage.

2. A curable composition as in claim 1, wherein said cyclic hydrocarbon moiety including an oxirane or thiirane group is a cycloaliphatic epoxy or episulfide, respectively, moiety.

3. A curable composition as in claim 1, wherein said aromatic ether moiety including an oxirane or thiirane group is an aromatic glycidyl or thioglycidyl ether, respectively, moiety.

4. A curable composition as in claim 1, wherein said compound is represented by the formula:

where R is selected from hydrogen, methyl, ethyl, propyl, isopropyl, butyl, isobutyl, tert-butyl, $C_{1-4}$ alkoxy, halogen, cyano, nitro and phenyl; each $R_1$ is independently selected from hydrogen, methyl, ethyl, propyl, and isopropyl; $R_2$ and $R_3$ are independently selected from hydrogen, methyl, ethyl, propyl, phenyl, tolyl, and benzyl; $R_4$ is independently selected from hydrogen, methyl, ethyl, propyl, isopropyl, butyl, isobutyl, tert-butyl, $C_{1-4}$ alkoxy, halogen, cyano, nitro and phenyl; p is an integer from 0–4; and X and Y are independently selected from O and S.

5. A curable composition as in claim 4, wherein said compound is selected from the group consisting of:

6. A thermosetting resin composition, reaction products of which are capable of softening and losing their adhesiveness under exposure to temperature conditions in excess of those used to cure the composition, said composition comprising:

(a) a curable resin component, at least a portion of which comprises a compound containing a cyclic hydrocarbon moiety including an epoxy or episulfide group and an aromatic ether moiety including an epoxy or episulfide group, said cyclic hydrocarbon moiety and said aromatic ether moiety being joined to each other through an oxycarbonyl-containing linkage or a thiocarbonyl-containing linkage;

(b) optionally, an inorganic filler component; and (c) a curing agent component comprising a member selected from the group consisting of anhydride compounds, amine compounds, amide compounds, imidazole compounds, and combinations thereof.

7. A thermosetting resin composition as in claim 6, wherein said cyclic hydrocarbon moiety including an epoxy or episulfide group is a cycloaliphatic epoxy or episulfide, respectively, moiety.

8. A thermosetting resin composition as in claim 6, wherein said aromatic ether moiety including an epoxy or episulfide group is an aromatic glycidyl or thioglycidyl ether, respectively, moiety.

9. A thermosetting resin composition as in claim 6, wherein said compound is represented by the formula:

where R is selected from hydrogen, methyl, ethyl, propyl, isopropyl, butyl, isobutyl, tert-butyl, $C_{1-4}$ alkoxy, halogen, cyano, nitro and phenyl; each $R_1$ is independently selected from hydrogen, methyl, ethyl, propyl, and isopropyl; $R_2$ and $R_3$ are independently selected from hydrogen, methyl, ethyl, propyl, phenyl, tolyl, and benzyl; $R_4$ is independently selected from hydrogen, methyl, ethyl, propyl, isopropyl, butyl, isobutyl, tert-butyl, $C_{1-4}$ alkoxy, halogen, cyano, nitro and phenyl; p is an integer from 0–4; and X and Y are independently selected from O and S.

10. A thermosetting resin composition as in claim 9, wherein said compound is selected from the group consisting of:

-continued

11. A thermosetting resin composition as in claim 6, wherein said curable resin component further comprises cycloaliphatic epoxy compounds, aromatic glycidyl ether compounds, and mixtures thereof.

12. The composition according to claim 6, further comprising a flowability agent.

13. The composition according to claim 12, wherein the flowability agent is a member selected from the group consisting of silanes, titanates, and combinations thereof.

14. The composition according to claim 6, further comprising an adhesion promoter.

15. The composition according to claim 14, wherein the adhesion promoter is a member selected from the group consisting of glycidyl trimethoxysilane, gamma-amino propyl triethoxysilane, and combinations thereof.

16. The composition according to claim 6, further comprising a cyanate ester.

17. The composition according to claim 6, wherein the inorganic filler component may be selected from the group consisting of materials constructed of or containing reinforcing silicas, aluminum oxide, silicon nitride, aluminum nitride, silica-coated aluminum nitride, boron nitride, and combinations thereof.

18. The composition according to claim 6, wherein the anhydride compounds of the curing agent component may be selected from the group consisting of hexahydrophthalic anhydride, methyl hexahydrophthalic anhydride, 5-(2,5-dioxotetrahydrol)-3-methyl-3-cyclohexene-1,2-dicarboxylic anhydride, and combinations thereof.

19. The composition according to claim 6, wherein the amine compounds of the curing agent component may be selected from the group consisting of dicyandiamide, diethylenetriamine, triethylenetetramine, diethylaminopropylariine, m-xylenediamine, diaminodiphenylamine, isophoronediamine, menthenediamine, polyamides, 4,4'-methylenedianiline, 4,4'-methylenebis(cyclohexylamine), and combinations thereof.

20. The composition according to claim 6, wherein the amide compounds of the curing agent component may be selected from the group consisting of dicyandiamide and combinations thereof.

21. The composition according to claim 6, wherein the imidazole compounds of the curing agent component may be selected from the group consisting of imidazole, isoimidazole, 2-methyl imidazole, 2-ethyl-4-methylimidazole, 2,4-dimethylimidazole, butylimidazole, 2-heptadecenyl-4-methylimidazole, 2-methylimidazole, 2-undecenylimidazole, 1-vinyl-2-methylimidazole, 2-n-heptadecylimidazole, 2-undecylimidazole, 2-heptadecylimidazole, 2-ethyl 4-methylimidazole, 1-benzyl-2-methylimidazole, 1-propyl-2-methylimidazole,

1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-guanaminoethyl-2-methylimidazole, addition products of an imidazole and trimellitic acid, addition products of an imidazole and 2-n-heptadecyl-4-methylimidazole, phenylimidazole, benzylimidazole, 2-methyl-4,5-diphenylimidazole, 2,3,5-triphenylimidazole, 2-styrylimidazole, 1-(dodecyl benzyl)-2-methylimidazole, 2-(2-hydroxyl-4-t-butylphenyl)-4,5-diphenylimidazole, 2-(2-methoxyphenyl)-4,5-diphenylimidazole, 2-(3-hydroxyphenyl)-4-,5-diphenylimidazole, 2-(p-dimethylaminophenyl)-4,5-diphenylimidazole, 2-(2-hydroxyphenyl)-4,5-diphenylimidazole, di(4,5-diphenyl-2-imidazole)-benzene-1,4,2-napnthyl-4,5-diphenylimidazole, 1-benzyl-2-methylimidazole, 2-p-methoxystyrylimidazole, and combinations thereof.

22. The composition according to claim 6, wherein the curing agent component is used in an amount of from about 3 to about 60 parts by weight, per 100 parts by weight of the curable resin.

23. The composition according to claim 12, wherein the flowability agent is selected from octyl trimethoxy silane, methacryloxy propyl trimethoxy silane, titanium IV tetrakis [2,2-bis[(2-propenyloxy)methyl]-1-butanolato-0] [bis(ditridecylphosphito-0), dihydrogen]$_2$, and combinations thereof.

24. The composition according to claim 6, wherein said composition is capable of sealing underfilling between a semiconductor device including a semiconductor chip mounted on a carrier substrate and a circuit board to which said semiconductor device is electrically connected.

25. A compound represented by the formula:

where R is selected from hydrogen, methyl, ethyl, propyl, isopropyl, butyl, isobutyl, tert-butyl, $C_{1-4}$ alkoxy, halogen, cyano, nitro and phenyl; each $R_1$ is independently selected from hydrogen, methyl, ethyl, propyl, and isopropyl; $R_2$ and $R_3$ are independently selected from hydrogen, methyl, ethyl, propyl, phenyl, tolyl, and benzyl; $R_4$ is independently selected from hydrogen, methyl, ethyl, propyl, isopropyl, butyl, isobutyl, tert-butyl, $C_{1-4}$ alkoxy, halogen, cyano, nitro and phenyl; p is an integer from 0–4; and X and Y are independently selected from O and S.

26. A compound as in claim 25, wherein said compound is selected from the group consisting of: